United States Patent
Wang et al.

(10) Patent No.: US 9,062,381 B2
(45) Date of Patent: Jun. 23, 2015

(54) METHOD FOR PROCESSING A SURFACE OF A METAL IMPLANT AND THE METAL IMPLANT PRODUCED BY THE METHOD

(75) Inventors: Wei-Ching Wang, Kaohsiung (TW);
Wei-The Chen, Kaohsiung (TW);
Wei-Jen Shih, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 659 days.

(21) Appl. No.: 13/339,630

(22) Filed: Dec. 29, 2011

(65) Prior Publication Data

US 2013/0087460 A1 Apr. 11, 2013

(30) Foreign Application Priority Data

Oct. 6, 2011 (TW) .............................. 100136303 A (51) Int. Cl.
| | | |
|---|---|---|
| *C25D 5/34* | (2006.01) | |
| *C25D 5/48* | (2006.01) | |
| *C25D 5/50* | (2006.01) | |
| *C25D 11/18* | (2006.01) | |
| *C25B 7/00* | (2006.01) | |
| *C25D 9/02* | (2006.01) | |

(52) U.S. Cl.
CPC ... *C25B 7/00* (2013.01); *C25D 5/50* (2013.01); *C25D 5/34* (2013.01); *C25D 9/02* (2013.01)

(58) Field of Classification Search
CPC .............. C25D 5/34; C25D 5/48; C25D 5/50; C25D 9/00; C25D 9/02
USPC ........................................ 205/206, 224, 229
See application file for complete search history.

(56) References Cited

U.S. PATENT DOCUMENTS

| | | |
|---|---|---|
| 5,965,006 A | 10/1999 | Baege et al. |
| 6,221,111 B1 | 4/2001 | Piveteau et al. |
| 7,635,447 B2 | 12/2009 | Hamman et al. |
| 7,758,909 B2 | 7/2010 | Ding |
| 2004/0091603 A1 | 5/2004 | Priewe |
| 2009/0124984 A1 | 5/2009 | Hanawa |
| 2009/0317443 A1 | 12/2009 | Willis et al. |

(Continued)

FOREIGN PATENT DOCUMENTS

| | | | | |
|---|---|---|---|---|
| KR | 2006077162 A | * | 7/2006 | .............. A61L 27/14 |
| TW | I385004 | | 2/2013 | |

OTHER PUBLICATIONS

Kenausis et al., "Poly(L-lysine)-g-Poly(ethylene glycol) Layers on Metal Oxide Surfaces: Attachment Mechanism and Effects of Polymer Architecture on Resistance to Protein Adsorption", J. Phys. Chem. B (no month, 2000), vol. 104, pp. 3298-3309.*

(Continued)

*Primary Examiner* — Edna Wong
(74) *Attorney, Agent, or Firm* — Alan D. Kamrath; Kamrath IP Lawfirm, P.A.

(57) ABSTRACT

A method for treating a surface of a metal implant includes a polishing step, a grafting step and a surface modifying step. The polishing step includes polishing a surface of a metal implant to remove an uneven, natural oxide layer on the surface of the metal implant and to generate an even oxide layer on the surface of the metal implant. The grafting step includes grafting an anti-adhesion macromolecule on an outer face of the even oxide layer. A covalent bond between the anti-adhesion macromolecule and oxygen atoms on the outer face of the even oxide layer is formed. Thus, a macromolecular anti-adhesion layer on the outer face of the even oxide layer can be created. The surface modifying step includes changing a property of the surface of the metal implant with the macromolecular anti-adhesion layer by high temperature and high pressure, providing the metal implant with high hydrophilicity.

6 Claims, 7 Drawing Sheets

(56) References Cited

U.S. PATENT DOCUMENTS

2009/0318622 A1* 12/2009 Migonney et al. ......... 525/326.6
2011/0160841 A1 6/2011 Wang et al.

OTHER PUBLICATIONS

Yao et al., "Anodization: A Promising Nano-Modification Technique of Titanium Implants for Orthopedic Applications", J. Nanosci. Nannotechnol. (no month, 2006), vol. 6, No. 9/10, pp. 2682-2692.*

Lincks et al., Response of MG63 osteoblast-like cells to titanium and titanium alloy is dependent on surface roughness and composition, Biomaterials, 1998, pp. 2219-2232, vol. 19, Elsevier Science Ltd.

Panagiotis G. Korovessis & Despina D. Deligianni, Role of Surface Roughness of Titanium Versus Hydroxyapatite on Human Bone Marrow Cells Response, Journal of Spinal Disorders & Techniques, 2002, pp. 175-183, vol. 15, Lippincott Williams & Wilkins, Inc., Philadelphia, U.S.

* cited by examiner

METHOD FOR PROCESSING A SURFACE OF A METAL IMPLANT AND THE METAL IMPLANT PRODUCED BY THE METHOD

BACKGROUND OF THE INVENTION

1. Field of the Invention

The present invention relates to a method for producing a metal implant and the metal implant produced by the method. More particularly, the present invention relates to a method for processing a surface of a metal implant to prevent adhesion with soft tissues and relates to the metal implant produced by the method.

2. Description of the Related Art

Metal implants are widely used in the medical fields and serve as temporary or permanent substitutes of damaged organs. The implants are rigid and generally in the form of a nail, screw, or plate made of titanium or steel. The metal implants must be bio-compatible to be accepted by the tissues of the bodies without causing any harm to the tissues.

However, a metal implant is fixed in a trauma of a body for a long period of time, such that adhesion is apt to occur between the metal implant and soft tissues surrounding the metal implant during recovery of the trauma, causing trouble in the removal of the metal implant after recovery of the trauma. Taking a bone trauma as an example, the trauma area of a patient is generally fixed by a bone plate or bone nail. After recovery of the trauma area by the growth of osteocytes, a second surgery is required to remove the bone plate or bone nail. During the recovery period, the surrounding soft tissues of the bone are apt to grow on the surface of the bone plate or bone nail and, thus, causing co-adhesion between the soft tissues and the bone plate or bone nail. The soft tissues must be scraped from the surface of the bone plate or bone nail before removing the bone plate or bone nail from the recovered trauma area in the second surgery. The cavities formed after removal of the bone plate or bone nail are difficult to heal in a short period of time, resulting in poor healing effect.

To avoid the adhesion between the metal implant and the surrounding soft tissues, U.S. Patent Publication No. 2009/0124984 A1 entitled "MEDICAL APPLIANCE AND PROCESS AND PROCESS FOR PRODUCING THE APPLIANCE" discloses a process including dipping a material for a medical appliance having a metal surface and an electrode into a solution including a hydrophilic organic compound having a polar group, and fixing the hydrophilic organic compound to the metal surface of the material for a medial appliance in accordance with an electrochemical grafting reaction by applying a voltage between a cathode and an anode using the material for a medial appliance as the cathode and the electrode as the anode. The hydrophilic organic compound can reduce the adverse affect resulting from the contact between the metal appliance and the human tissues.

However, the layer of hydrophilic organic compound formed on the metal surface of the metal appliance after the electrochemical reaction (electrochemical grafting) is often uneven due to unevenness of the metal surface. Furthermore, the non-processed metal surface exhibits an uneven oxidation status. Thus, the number of the oxygen atoms is often insufficient for bonding with the free hydrophilic organic compound moved to the metal surface. The efficiency and quality of the electrochemical grafting are limited, failing to provide the most effective result of electrochemical grafting on the metal surface of the metal appliance.

Furthermore, the hydrophilic organic compound directly formed on the metal surface of the metal appliance can not be reliably bonded to the metal surface, such that the electrochemical grafting result is incomplete after use of the metal appliance in the human body. The desired lubricating (anti-adhesion) effect during use of the metal appliance is significantly and adversely affected. Thus, the quality of the electrochemical grafting of the organic compound is risky.

Thus, a need exists for a novel method for treating a surface of a metal implant to effectively enhance the efficiency and quality of electrochemical grafting of an organic compound on the surface of the metal implant.

SUMMARY OF THE INVENTION

An objective of the present invention is to provide a method for processing a surface of a metal implant to increase the uniformity of oxidation of the surface of the metal implant, assuring the efficiency and quality of the electrochemical grafting of the organic compound.

Another objective of the present invention is to provide a method for processing a surface of a metal implant to increase the hydrophilicity of the organic compound to enhance the anti-adhesion effect of the metal implant to the soft tissues.

The present invention fulfills the above objectives by providing a method for treating a surface of a metal implant. The method includes a polishing step, a grafting step and a surface modifying step. The polishing step includes polishing a surface of a metal implant to remove an uneven, natural oxide layer on the surface of the metal implant and to generate an even oxide layer on the surface of the metal implant. The electrochemical grafting step includes electrochemical grafting an anti-adhesion macromolecule on an outer face of the even oxide layer, forming a covalent bond between the anti-adhesion macromolecule and oxygen atoms on the outer face of the even oxide layer, and performing a macromolecular anti-adhesion layer on the outer face of the even oxide layer. The surface modifying step includes changing a property of the surface of the metal implant with the macromolecular anti-adhesion layer by high temperature and high pressure, providing the metal implant with high hydrophilicity.

A metal implant produced from the method includes a metal layer, an oxide layer formed on a surface of the metal layer, and a macromolecular anti-adhesion layer formed on an outer surface of the oxide layer. The macromolecular anti-adhesion layer is formed of polyethylene glycol.

The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

The present invention provides a method for producing a metal implant with high hydrophilicity. The metal implant includes a surface having an electrochemical graft layer of an organic compound with high evenness. The organic compound is an anti-adhesion macromolecule. The metal implant can be electrically conductive. Preferably, the metal implant is made of a metal including titanium (such as pure titanium or titanium alloy) or stainless steel.

Figure 1:
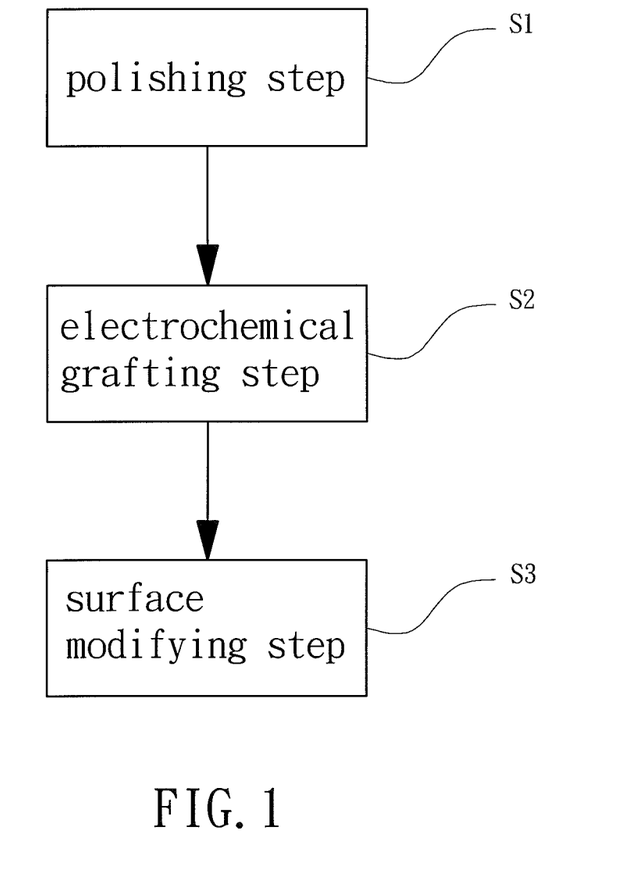
FIG. 1 shows a flowchart illustrating a method for processing a surface of a metal implant according to the present invention.

FIG. 1 shows an example of a method for treating a surface of a metal implant according to the present invention. The method includes a polishing step S1, an electrochemical grafting step S2, and a surface modifying step S3.

In the polishing step S1, a surface of a metal implant is polished to remove an uneven, natural oxide layer on the surface of the metal implant and to generate an even oxide layer on the surface of the metal implant. More specifically, a natural oxide layer is liable to be formed on the surface of the metal implant in a natural environment. The natural oxide layer generally has a thickness of 10 nm and has insufficient evenness, such that the natural oxide layer is too uneven to be used in the subsequent electrochemical grafting step S2. Thus, the surface of the metal implant is polished to remove the uneven, natural oxide layer from the surface of the metal implant, and a new, even oxide layer is generated after the evenness of surface of the metal implant is improved by polishing. The even oxide layer is suitable for the subsequent electrochemical grafting step S2. The polishing can be mechanical polishing, electropolishing, or polishing through submersion in hydrogen peroxide. Preferably, the polishing is electropolishing to remove the uneven, natural oxide layer on the surface of the metal implant and to generate an even oxide layer of an appropriate thickness on the surface of the metal implant. The electropolishing can be applied to the three-dimensional surface of the metal implant without the disadvantage of generation of stress resulting from mechanical polishing, such as using a cylindrical grinder. The surface of the metal implant after electropolishing exhibits an even sheen like a mirror. Furthermore, the even oxide layer can be gradually formed during the supply of a stable electric current.

In an example of electropolishing, a titanium-based metal implant is placed on an anode and submerged in a first electrolyte including hydrofluoric acid. The first electrolyte is supplied with an electric current having a density of 0.2-2 $A/dm^2$ and, particularly, 0.5 $A/dm^2$. The metal implant at the anode continuously dissolves. The titanium-based metal implant undergoes electropolishing for 5-60 minutes. The uneven portions on the surface of the metal implant are removed while removing the uneven, natural oxide layer. Preferably, the titanium-based metal implant undergoes electropolishing for 15 minutes. When the even oxide layer can reflect like a mirror, the even oxide layer has an outer face with the best evenness for the subsequent electrochemical grafting step S2. The first electrolyte can be any solution capable of dissolving the metal implant at the anode, such as, but not limited to, hydrofluoric acid. The outer face of the even oxide layer faces away from the metal layer and has an average roughness of 0.01-0.8 μm.

In the electrochemical grafting step S2, an anti-adhesion macromolecule is electrochemically grafted on the outer face of the even oxide layer, forming a covalent bond between the anti-adhesion macromolecule and oxygen atoms on the outer face of the even oxide layer, such that a macromolecular anti-adhesion layer on the outer face of the even oxide layer is created. Specifically, in an example of the electrochemical grafting step, a cathodic treatment is used, the metal implant with the even oxide layer is placed on a cathode, and the cathode is submerged in a second electrolyte. After the second electrolyte is supplied with an electric current having a density of 10-200/$dm^2$, the covalent bond between the anti-adhesion macromolecule and the oxygen atoms on the outer face of the even oxide layer can be formed, forming the macromolecular anti-adhesion layer on the outer face of the even oxide layer until a thickness of the macromolecular anti-adhesion layer is 1-35 nm. At this time, the macromolecular anti-adhesion layer possesses good evenness and uniformity. Thus, a metal implant with an even oxide layer and a macromolecular anti-adhesion layer is obtained. Preferably, the anti-adhesion macromolecule is polyethylene glycol. Preferably, the second electrolyte includes polyethylene glycol and an alkaline solution. In an example, polyethylene glycol of 1-10M % is dissolved in the alkaline solution that is a sodium chloride solution. The pH value of the alkaline solution is preferably smaller than 11 to maintain a better suspending effect for the anti-adhesion macromolecule.

In an example, the metal implant with the even oxide layer is placed on an anode and submerged in the second electrolyte including polyethylene glycol. After the second electrolyte is supplied with an electric current of 135 amperes, the polyethylene glycol is dissociated and moves to the face of the metal implant and forms an even covalent bond with the oxygen atoms on the outer face of the even oxide layer, gradually forming an anti-adhesion layer of polyethylene glycol on the outer surface of the even oxide layer. The metal implant with the even oxide layer undergoes the formation of the anti-adhesion layer of polyethylene glycol for 5-60 minutes. Then, the surface modifying step S3 is carried out.

In the surface modifying step S3, the property of the surface of the metal implant with the macromolecular anti-adhesion layer is changed by high temperature and high pressure, providing the metal implant with high hydrophilicity. Specifically, the surface of the metal implant with the macromolecular anti-adhesion layer has an insufficient hydrophilicity and, thus, may cause adverse affect to the uniform bonding strength between the macromolecular anti-adhesion layer and the metal implant. In an example, the metal implant with the macromolecular anti-adhesion layer is placed in a high temperature and high pressure environment to change the hydrophilicity of the surface. The contact angle of the surface of the metal implant is changed from 60° to 40°. It is, thus, confirmed that the hydrophilicity of the surface of the metal implant is significantly increased, enhancing the uniform bonding strength between the macromolecular anti-adhesion layer and the metal implant. In an example, the metal implant with the macromolecular anti-adhesion layer is placed in a hyperbaric chamber having a temperature in a range of 120-135° C. and a pressure in a range of 1.5-40 $kg/cm^2$ to change the hydrophilicity of the surface of the metal implant. A metal implant with high hydrophilicity is, thus, obtained.

Figure 2:
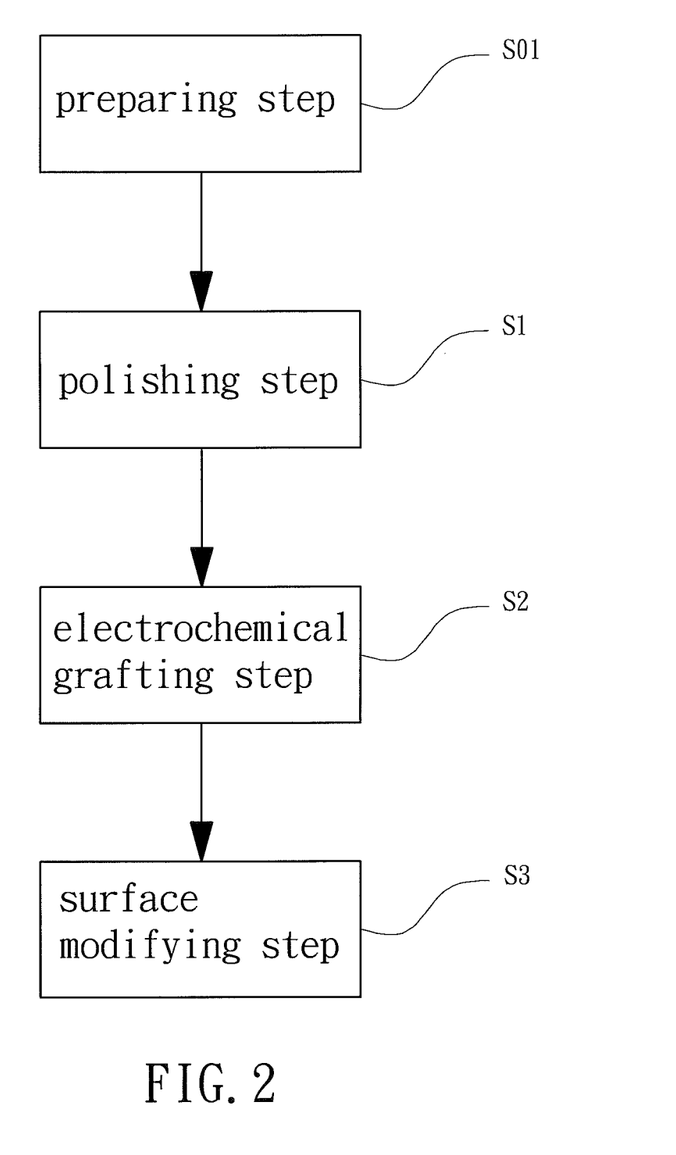
FIG. 2 shows a flowchart illustrating another example of the method according to the present invention.

With reference to FIG. 2, a preparing step S01 can be carried out before the polishing step S1. The preparing step S01 includes washing out impurities on the surface of the metal implant. In an example, the metal implant is submerged in deionized water and sonicated for 5-10 minutes to accomplish the first-stage cleaning. Then, the metal implant is placed in a solution of acetone and subjected to $2^{nd}$-time sonication for 5-10 minutes. Then, the metal implant is washed and moistened with deionized water, accomplishing the second-stage cleaning. Finally, the metal implant is placed in an alcoholic solution and subjected to $3^{rd}$-time sonication for 5-10 minutes, accomplishing the third-stage cleaning. The substances (such as dirt, dust, or oil) adhered to the surface of the metal implant can, thus, be completely removed before the polishing step S1. This can enhance the bonding strength between the even oxide layer and the surface of the metal implant.

Figure 3:
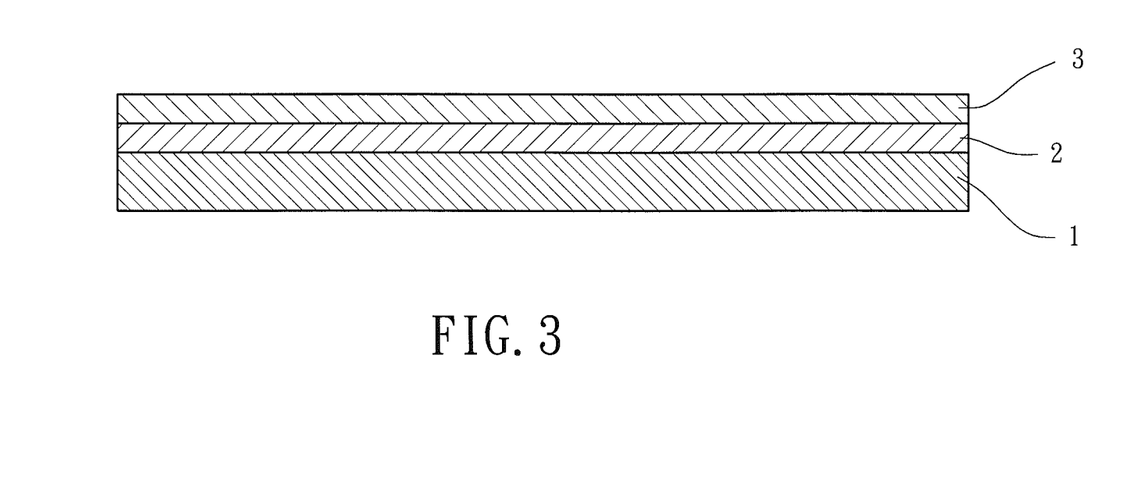
FIG. 3 shows a cross sectional view of a metal implant according to the present invention.

After the above polishing and electrochemical grafting, a metal implant is obtained. With reference to FIG. 3, the metal implant includes a metal layer 1, an oxide layer 2, and a macromolecular anti-adhesion layer 3. The oxide layer 2 is formed on the surface of the metal layer 1. The macromolecular anti-adhesion layer 3 is formed on an outer face of the even oxide layer 2 facing away from the metal layer 1. The metal layer 1 after polishing exhibits better evenness, such that the average roughness of the outer face of the oxide layer can be reduced to be 0.01-0.8 μm. Preferably, the surface thickness deviation of the metal layer is 0-10 nm, such that the oxide layer 2 exhibits a uniform, compact state, while the oxide layer 2 is formed on the surface of the metal layer 1. This enhances the efficiency of the electrochemical graft between the anti-adhesion macromolecule of the macromolecular anti-adhesion layer 3 and the oxygen atoms on the oxide layer 2, obtaining the macromolecular anti-adhesion layer with high evenness. The metal layer 1 can be electrically conductive. Preferably, the metal includes titanium (such as pure titanium or titanium alloy) or stainless steel. In an example, the metal layer 1 is titanium oxide having an average roughness of 0.01-0.8 μm, preferably 0.1 μm, to maintain the efficiency of electrochemical graft between the oxygen atoms on the surface of the oxide layer 2 and the anti-adhesion macromolecule. Preferably, the macromolecular anti-adhesion layer is formed by electrochemical grafting of polyethylene glycol and preferably has a thickness of 1-50 nm and, more preferably, of 1-35 nm. Due to the macromolecular anti-adhesion layer 3, the metal implant possesses an enhanced anti-adhesion effect to soft tissues.

In the metal implant with high hydrophilicity produced according to the present invention, the even oxide layer 2 is formed on the surface of the metal layer 1 by the above-mentioned polishing step S1, forming a covalent bond between the anti-adhesion macromolecule and the oxygen atoms on the outer face of the even oxide layer 2 in an even and highly efficient manner. Thus, the outer face of the even oxide layer 2 has high evenness, and the macromolecular anti-adhesion layer 3 is more uniform and compact. A metal implant with high hydrophilicity is obtained after the surface modifying step S3. The metal implant can be used as an implant in a human body. In a case of a bone plate or bone nail of titanium alloy, through provision of the macromolecular anti-adhesion layer with high evenness and high uniformity, the soft tissues surrounding the bone plate or bone nail are less apt to grow on the surface of the bone plate or bone nail, avoiding adhesion between the soft tissues and the bone plate or bone nail. Thus, in a second surgery for removing the bone plate or bone nail for a patient having a bone trauma, it is not necessary to proceed with an operation for removing the soft tissues from the surface of the bone plate or bone nail. As a result, the bone plate or bone nail can easily be removed from the recovered trauma area. Since the metal implant provides an enhanced anti-adhesion effect to the soft tissues, the time for removing the soft tissues from the surface of the bone plate or bone nail can be saved, while maintaining the normal growing speed of the osteocyte after the surgery. Thus, the speed and completeness of post-surgery healing can be assured.

In order to prove the metal implant according to the present invention can be obtained through the above-mentioned method in which the macromolecular anti-adhesion layer 3 with high evenness and high uniformity is formed on the outer surface of the even oxide layer 2 (for the purposes of preventing adhesion between the metal implant and the surrounding soft tissues in the trauma area) after the even oxide layer 2 is formed on the metal layer 1, the metal implant was compared to the current products available in the market. An oxide layer was formed on each current product by anodizing, and an anti-adhesion macromolecule was electrochemical grafted on the oxide layer. The adhesion between the fibroblasts and the soft tissues and the growth of the osteoblasts were analyzed. The results were shown in FIGS. 4, 5, 6 and 7.

Figure 4:
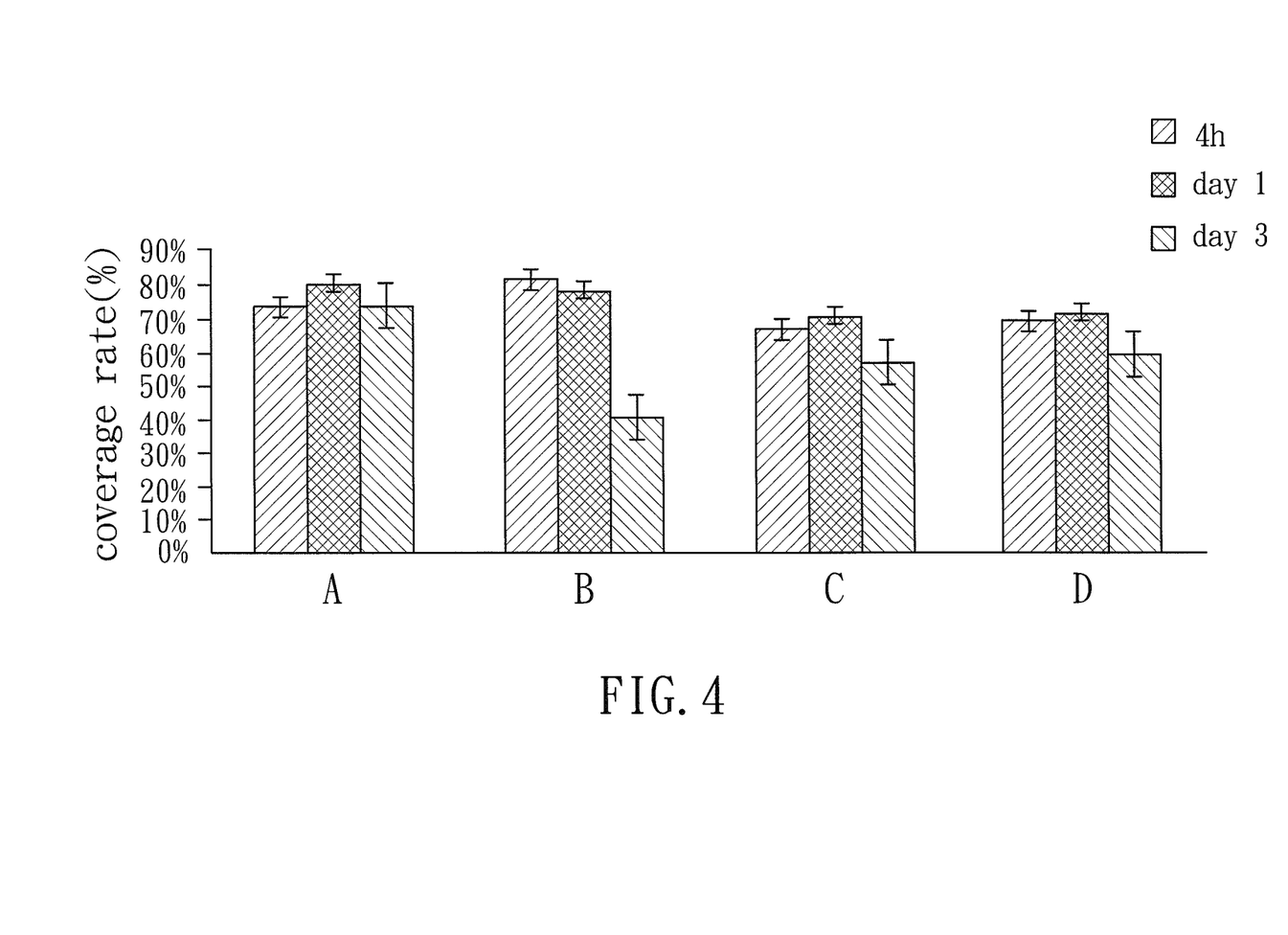
FIG. 4 is a diagram showing coverage of fibroblasts.

FIG. 4 shows coverage of the fibroblasts on the surface of the metal implant. Sample A was a test plate of titanium alloy polished by the method of the present invention and including an even oxide layer. Sample B was a test plate of titanium alloy polished by the method of the present invention, and a macromolecular anti-adhesion layer with high evenness and high uniformity was formed on the even oxide layer. Sample C was a golden test plate of a titanium alloy that was obtained by anodizing a current product and that included a natural oxide layer. Sample D was a golden test plate of titanium alloy that was obtained by anodizing a current product, and an anti-adhesion macromolecule was electrochemical grafted on the natural oxide layer. The anti-adhesion effect relative to the soft tissues was demonstrated with the coverage of L929 fibroblasts.

TABLE 1

| | A | B | C | D |
|---|---|---|---|---|
| 4 hours | 74.33% | 81.78% | 67.73% | 68.99% |
| Day 1 | 81.03% | 78.29% | 70.85% | 71.88% |
| Day 3 | 74.24% | 41.31% | 57.61% | 59.10% |

As can be seen from FIG. 4 and Table 1, the coverage rate of the fibroblast on the sample C on the third day was 57.61%, and the coverage rate of the fibroblast on the sample B on the third day was 41.31%. It is, thus, proven that the current product after anodizing can have reduced adhesion to the soft tissues. However, the anti-coverage rate of the current product can only maintain about 57%. Namely, the coverage rate of the metal implant can not be further effectively reduced. The coverage rate of the fibroblast on the sample D on the third day was close to the sample without electrochemical grafting of the anti-adhesion macromolecule. The coverage rate of the fibroblast on the sample B on the third day was significantly reduced to 41.31%, which proved that the even oxidation of the surface of the metal implant can be increased after the polishing step S1. The efficiency and quality of grafting of the anti-adhesion macromolecule are effectively improved, effectively reducing the coverage of the L929 fibroblasts on the surface of the metal implant.

Figure 6:
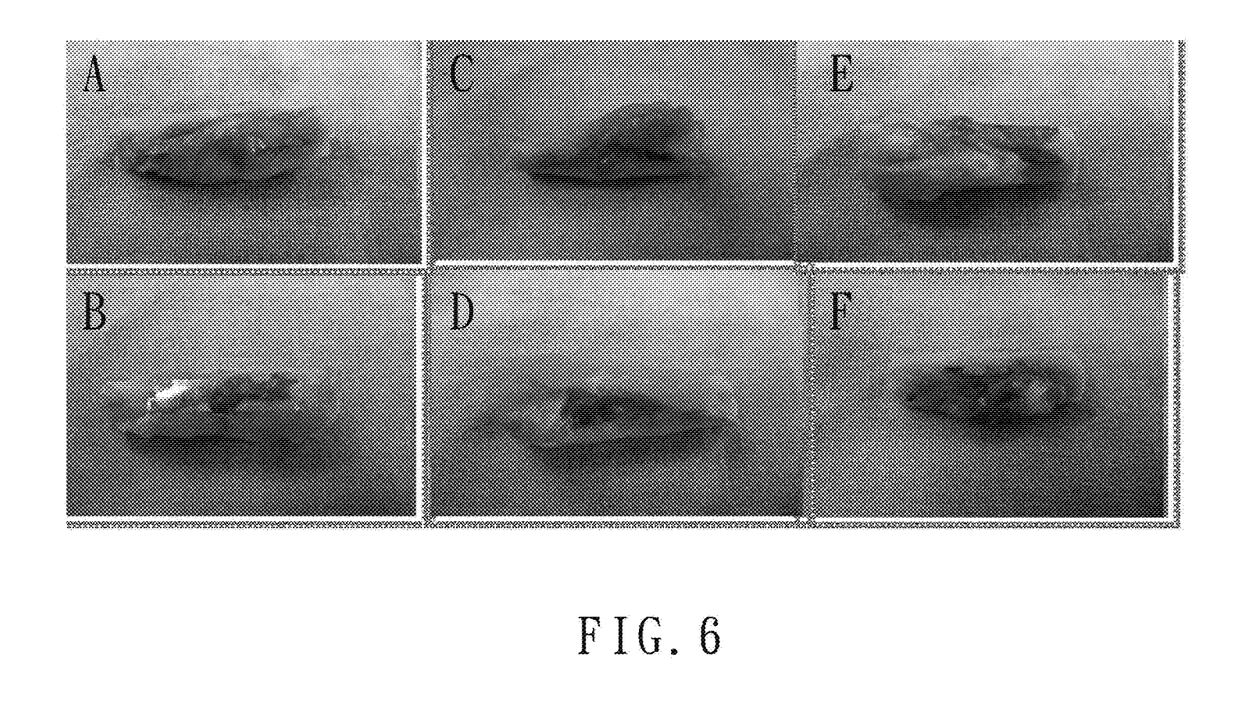
FIG. 6 shows adhesion of soft tissues using the metal implants according to the present invention.

FIG. 6 shows experimental results on shank bones of experimental animals. Each of samples A-F was implanted into a shank bone of an experimental animal, with three holes of 1.5 mm drilled in the shank bones. The samples A-F were removed after four weeks to analyze the adhesion of the soft tissues on the surfaces of the test plates of titanium alloy. Sample E was a test plate of titanium alloy processed by hydrogen peroxide and including an even oxide layer. Sample F was a test plate of titanium alloy processed by hydrogen peroxide, and a macromolecular anti-adhesion layer with high evenness and high uniformity was formed on the even oxide layer.

As can be seen from FIG. 6, in the demonstrated bone trauma environment in which the tissue fluid of the injured bone overflowed and generated a large amount of adhesion, sample F included properties of attracting osteocyte to cover its surface and, thus, could not provide the anti-adhesion effect to the soft tissues in the bone trauma environment. Regardless of receiving grafting of an anti-adhesion macromolecule, the anti-adhesion effect to the soft tissues provided by the current products was apparently insufficient. Due to electrochemical grafting of the uniform anti-adhesion macromolecule after polishing, sample B has no osteocyte covered on its surface. Thus, more than 75% of the surface of sample B was not adhered by the soft tissues. As a result, the metal implant provided an enhanced anti-adhesion effect to the soft tissues.

Figure 5:
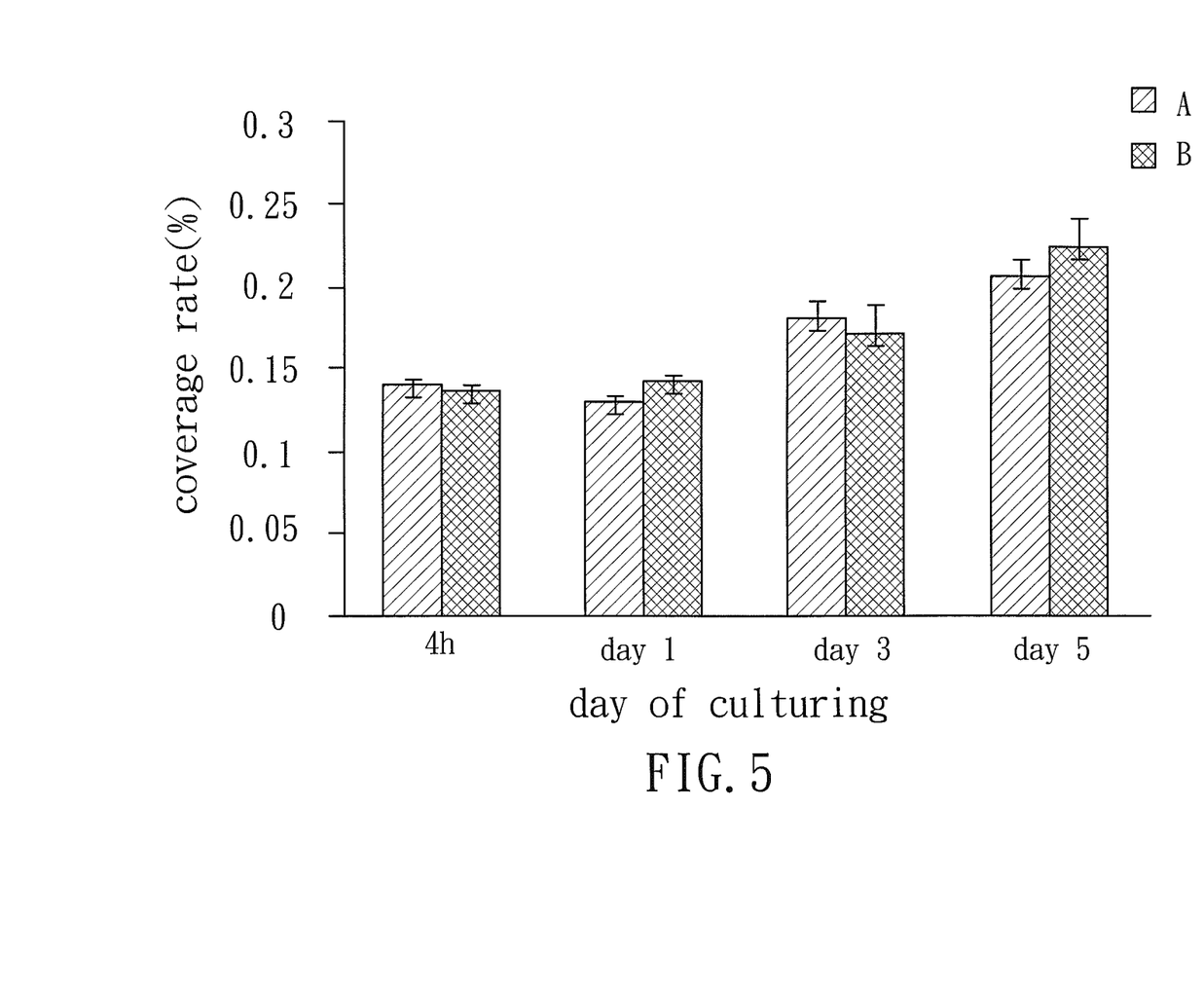
FIG. 5 is a diagram showing growth of osteocyte.

FIG. 5 shows growth of osteoblasts on surfaces of metal implants. Specifically, MG-63 osteoblasts were cultivated on samples A and B to analyze the optical density (OD value) of the osteocyte at different times. The optical density exhibited the growing speed of the osteocyte at different times to indicate the affect to the osteocyte by the anti-adhesion macromolecule electrochemically grafted on the metal implant.

As can be seen from FIG. 5, in either sample A or sample B, the growing speed of the cells was increased in proportion to the time. It is, thus, confirmed that the anti-adhesion macromolecule does not affect the growth of the osteoblasts nor induce the proliferation of osteo-tissues.

Figure 7:
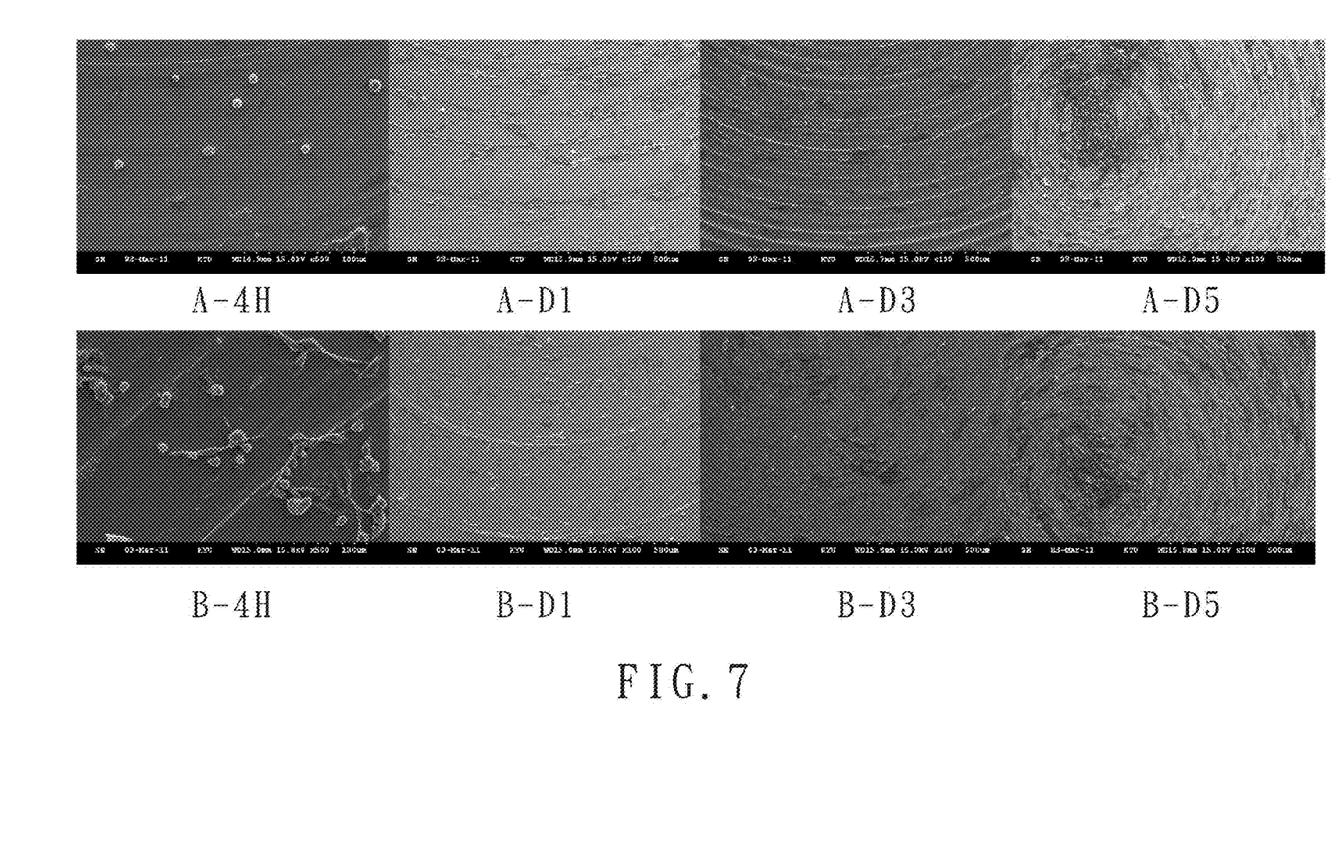
FIG. 7 shows growth patterns of the osteocyte using the metal implants according to the present invention.

FIG. 7 shows pictures of samples A and B by a scanning electron microscope. After four hours, the osteoblasts rapidly adhere on sample B, showing that the surface of the test plate of titanium alloy had higher hydrophilicity. However, the osteocyte on both samples A and B had no differences in cell morphology, showing that the macromolecular anti-adhesion layer did not adversely affect the growing speed of the osteoblasts. Thus, the metal implants according to the present invention can assure the speed and effect of recovery in the bone trauma area.

The method for processing a surface of a metal implant according to the present invention can increase the evenness of oxidation on the surface of the metal implant to improve the efficiency and quality of electrochemical grafting of an organic compound.

The method for processing a surface of a metal implant according to the present invention can increase the hydrophilicity of the organic compound on the surface of the metal implant to enhance the anti-adhesion effect of the metal implant to soft tissues.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method for treating a surface of a metal implant, comprising:
    polishing a surface of a metal implant to remove an uneven, natural oxide layer on the surface of the metal implant and to generate an even oxide layer on the surface of the metal implant;
    electrochemical grafting an anti-adhesion macromolecule which is an organic compound on an outer face of the even oxide layer, with a covalent bond forming between the anti-adhesion macromolecule and oxygen atoms on the outer face of the even oxide layer, creating a macromolecular anti-adhesion layer on the outer face of the even oxide layer; and
    changing a property of the surface of the metal implant with the macromolecular anti-adhesion layer by high temperature and high pressure, providing the metal implant with high hydrophilicity.

2. The method claimed in claim 1, wherein the said polishing the surface comprises electropolishing the surface, with the metal implant placed on an anode and submerged in a first electrolyte supplied with an electric current having a density of 0.2-2 $A/dm^2$, removing the uneven, natural oxide layer from the surface of the metal implant and generating the even oxide layer, with the outer face of the even oxide layer having an average roughness of 0.01-0.8 μm.

3. The method as claimed in claim 2, wherein the first electrolyte includes a solution of hydrofluoric acid.

4. The method as claimed in claim 2, wherein the said electrochemical grafting comprises placing the metal implant with the even oxide layer on a cathode and submerging the cathode in a second electrolyte supplied with an electric current having a density of 10-200/$dm^2$, forming the covalent bond between with the anti-adhesion macromolecule and the oxygen atoms on the outer face of the even oxide layer to form the macromolecular anti-adhesion layer, wherein the second electrolyte includes polyethylene glycol and an alkaline solution.

5. The method as claimed in claim 4, wherein the alkaline solution is a sodium chloride solution.

6. The method as claimed in claim 4, wherein the high temperature is in the range of 120-135° C., wherein the high pressure is in the range of 1.5-40 $kg/cm^2$.

* * * * *